United States Patent [19]

Wyatt et al.

[11] Patent Number: 4,508,123
[45] Date of Patent: Apr. 2, 1985

[54] THERMODILUTION INJECTATE ASSEMBLY

[75] Inventors: Philip W. Wyatt, La Canada; Allen L. Newsome, Jr., Culver City; William G. Bloom, Northridge; Bernard Siegel, Los Angeles; Michael Lubov, Arcadia, all of Calif.

[73] Assignee: American Hospital Supply Corporation, Evanston, Ill.

[21] Appl. No.: 499,938

[22] Filed: Jun. 1, 1983

[51] Int. Cl.³ .................................................. A61B 5/02
[52] U.S. Cl. ....................................... 128/692; 128/713
[58] Field of Search ............... 128/692, 713, 736, 399, 128/400, DIG. 3; 604/32, 65, 66, 113, 114, 248; 165/11 R, 46, 96

[56] References Cited

U.S. PATENT DOCUMENTS

| | | | |
|---|---|---|---|
| 3,612,059 | 10/1971 | Ersek | 604/113 |
| 4,177,816 | 12/1979 | Torgeson | 128/400 |
| 4,210,173 | 7/1980 | Choksi et al. | 604/186 |
| 4,281,665 | 8/1981 | Gezari | 128/713 |
| 4,416,280 | 11/1983 | Carpenter et al. | 604/113 |

Primary Examiner—Kyle L. Howell
Assistant Examiner—Ruth Smith
Attorney, Agent, or Firm—Roger A. Williams

[57] ABSTRACT

A thermodilution injectate assembly which includes a length of flexible tubing for introducing fluid from a solution container to the assembly. An insulated container which holds a heat exchange medium and into which is positioned a substantially flat plate heat exchanger. The heat exchanger includes an inlet port and an outlet port and a fluid-flow path therebetween, which path provides a heat exchange relationship between fluid flowing through the path and the heat exchange medium. A dual directional valve is connected to the outlet port of the heat exchanger and to the solution container. A three-ported stopcock is in fluid-flow communication with the dual directional valve. A syringe is connected to a port on the three-ported stopcock and a length of flexible tubing is connected to a port on the three-ported stopcock for delivering the cooled fluid to a patient for monitoring the cardiac output. The flexible tubing can be connected to a catheter which is inserted in the patient, which catheter includes a temperature probe.

39 Claims, 5 Drawing Figures

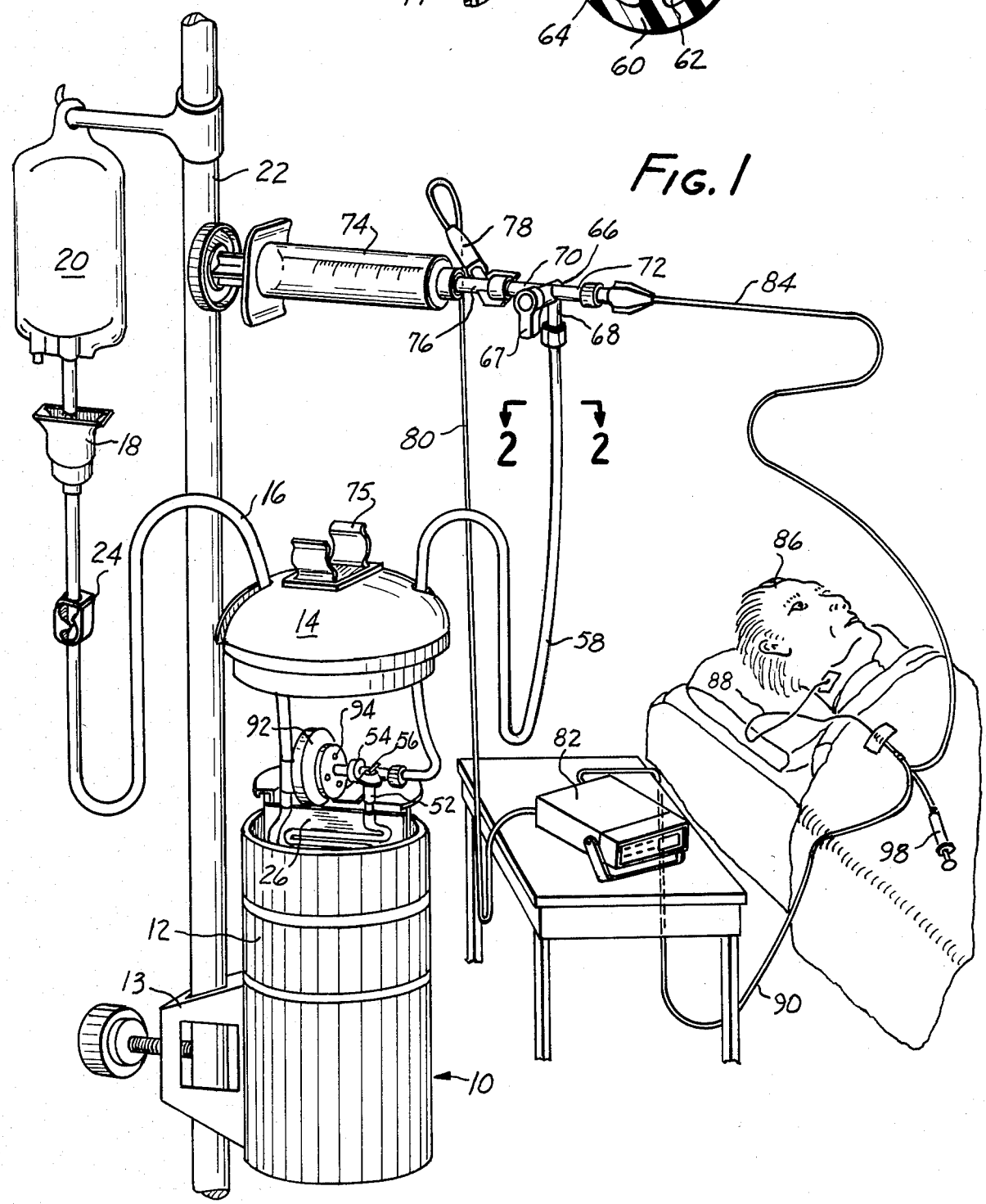

THERMODILUTION INJECTATE ASSEMBLY

BACKGROUND OF THE INVENTION

The invention herein is directed to an assembly for providing sterile chilled diluent for use in thermodilution procedures for determining cardiac output.

Cardiac output, defined as the volumetric flow rate of blood through the heart (usually in liters per minute), is a critical parameter in determining the state of health of the critically ill patient, especially those who have suffered a significant cardiac insult such as major cardiac surgery or acute myocardial infarction ("heart attack"). Studies have indicated that a typical cardiac patient will have this procedure performed approximately 30 times during their hospitalization.

The earliest method for determining cardiac output was the Fick method which measured the cardiac output value indirectly by measuring the body's oxygen rate of uptake and dividing this by the difference in oxygen concentration in the arterial and nervous sides of the circulatory system. This method had certain built-in inaccuracies and required waiting for the laboratory to determine the blood oxygen concentrations. The cost of analysis and the need for more rapid results led to the development of two invasive dilution techniques, dye dilution and thermal dilution. In both techniques a catheter is inserted into the flow region. In the dye dilution technique, a dye of known concentration is released in the blood stream and is sampled downstream. The amount of dilution is measured using a colorimeter. The flow rate can be calculated using the Stewart-Hamilton equation.

The thermal dilution technique, first introduced in 1971 by Drs. Swan and Ganz, replaced the dye injection with a bolus of fluid which is at a known temperature, significantly lower than the blood temperature and the downstream "thermal" dilution is monitored with a temperature sensor imbedded in the catheter. Because all of the measured variables are electrical in nature, the output from the thermodilution temperature sensor and the temperature of the injectate can be monitored by a small dedicated computer which uses a modified form of the Stewart-Hamilton equation to calculate and display the cardiac output within a minute of the injection of the bolus. This technique has become the method of choice for determining cardiac output because of the ease of use and the rapid display of the test results.

The modified Stewart-Hamilton equation is of the form:

$$C.O. = \frac{1.08 \, (60) \, C_T \, V_I \, (T_B - T_I)}{\int T_B(t) \, dt}$$

where:

$$1.08 = \frac{C_p(5 \text{ percent dextrose})}{C_p(\text{Blood})}$$

The ratio of the density times the specific heat of 5 percent dextrose to the density times the specific heat of the blood.

$C_T$ = Correction factor for the injectate temperature rise through the catheter.
60 = Seconds/minute.
$V_I$ = Volume of injectate in liters.
$T_B$ = Initial blood temperature in °C.
$T_I$ = Initial injectate temperature in °C.
$\int T_B(t) dt$ = Area under the time-temperature thermodilution curve in °C.-sec.

Careful analysis of the equation will show that to maximize accuracy of the analysis: (1) $T_I$ should be as low as possible to maximize the term $(T_B-T_I)$; (2) $T_I$ must be known as accurately as possible. Initial methods to achieve these two objectives involved either: (1) prefilling syringes and soaking them in an ice bath (for up to one hour) and monitoring the temperature of the ice bath as an indication of the syringe temperature; or (2) drawing syringes from a sterile beaker full of fluid that has been allowed to sit in an ice bath until thoroughly chilled. Again the ice bath temperature was used as an indication of the injectate temperature.

As is apparent and readily appreciated, there exists a potential for significant inaccuracies in the value for $T_I$. Differences between bath temperature (measured) and the syringe temperature (actual), combined with the fact that the syringe rapidly changes temperature after it leaves the ice bath, indicate the need to measure the injectate temperature precisely at the time of injection.

Other factors also dictate the need for an improved technique and assembly. Because the procedure may be performed in excess of 30 times on a single patient and each performance requires 3 to 5 separate injections, there is a significant need to reduce the potential for contaminating the patient with bacteria introduced while manipulating the solutions. Two critical times for such potential contamination are the steps involved in prefilling the syringes and the connection and disconnection of the syringes to the catheter at the time of use. Because the syringes and ice bath must be prepared 45 minutes to one hour prior to performing the procedure to adequately chill the injectate, either a continuous supply of such prefilled syringes must be maintained for emergencies or the test must be delayed.

It would be desirable to provide an assembly which would overcome the various shortcomings indicated for the current systems. It would be desirable to provide an assembly which would be ready to use immediately upon charging the cooling bath with ice; wherein the rate at which chilled solution can be withdrawn is significantly greater than current coil designs; which could be pre-chilled, removing the warm solution from the lines, without opening the system to contamination; wherein temperature of injection $T_I$ is maintained nearly at 0° C. up to the catheter injection port; and which includes a rugged, totally disposable, in-line temperature probe.

SUMMARY OF THE INVENTION

The invention herein is directed to an assembly for use in a thermodilution technique for monitoring cardiac output. The assembly includes a length of flexible tubing having a puncture spike connected at one of its ends for providing a connection to a solution container such as an intravenous (IV) solution container, whether rigid or flexible. The other end of the flexible tubing leads to an insulated container which holds the heat exchange medium for exchanging heat with the fluid to be administered to a patient. Generally, such a heat exchange medium can be ice or an ice bath. Within the insulated container is a substantially flat plate heat exchanger which includes an inlet port and an outlet port. The end of the flexible tubing leading from the solution container is attached to the inlet port.

The flat plate heat exchanger includes a tortuous path through which a fluid can flow while being in heat exchange relationship with the heat exchange medium in the insulated container. The flat plate heat exchanger can be a laminated structure wherein one layer of the laminate is a metal material across which heat exchange can occur. The metal layer can be contoured to provide a fluid-flow path between the layers in the laminated structure. Another layer of the laminated structure can be a plastic or can be another metal surface. The layers of the laminate can be sealed together to provide a fluid-tight seal. The second layer can also be contoured to provide a fluid-flow path such that when the two layers are bonded together the contoured fluid-flow paths on each layer of the laminated structure coincide to provide one fluid-flow pathway through the laminated structure.

The outlet port on the flat plate heat exchanger is connected in fluid-flow communication to a dual acting or dual directional valve. The dual directional valve is a three-ported valve body structure which can direct fluid flow to the patient or provide a path for fluid to be returned to the solution container. The three-ported valve body structure includes a first port having a valve positioned therein for permitting fluid flow into the valve body and preventing fluid flow out of the valve body. A second port on the three-ported valve body has a valve positioned therein for permitting fluid flow out of the valve body and preventing fluid flow into the valve body. The third port on the valve body does not contain a valve and thereby permits fluid flow into or out of the valve body.

A filter can be provided between the second port on the dual directional valve body and the flexible tubing leading to the inlet port of the flat plate heat exchanger to provide a filtering of the fluid being returned to the solution container.

A length of insulated flexible tubing is connected to the third port on the dual directional valve. The insulated flexible tubing provides for substantially maintaining the temperature of the fluid as it flows along the tubing. The insulated tubing is connected to a port of a three-ported stopcock. A syringe is connected to one of the other ports of the three-way stopcock. The syringe is insulated by providing a dead air space between the syringe barrel and an outer barrel covering. Another length of flexible tubing can be connected to the remaining port of the three-ported stopcock. Such flexible tubing can also be insulated. The length of flexible tubing extends to the protruding end of a catheter which is inserted into the circulatory system of a patient. The catheter can be connected directly to the three-ported stopcock. The lead from the catheter which is inserted in the patient can extend to a display unit or a monitor. A temperature probe can be positioned along the fluid-flow path in the assembly to sense the temperature of the fluid after having been in a heat exchange relationship with the heat exchange medium. The temperature probe can be inserted in the assembly between the three-ported stopcock and the syringe to monitor the temperature of the solution as it is being injected into the circulatory system of the patient.

BRIEF DESCRIPTION OF THE DRAWINGS

The assembly herein for use in a thermodilution technique for measuring cardiac output will be better understood with regard to the following description and the accompanying drawings wherein:

FIG. 1 is a schematic representation of the assembly herein partially shown in an exploded view;

FIG. 2 is a cross-sectional view along the insulated tubing illustrated in FIG. 1 and along lines 2—2 of FIG. 1;

FIG. 4 is a partial cross-sectional view of the heat exchanger assembly shown in FIG. 3 taken along lines 4—4; and FIG. 5 is a corresponding partial cross-sectional view of another embodiment of a heat exchanger assembly which would correspond to the view taken along FIG. 4—4 of FIG. 3.

DETAILED DESCRIPTION

Figure 3:
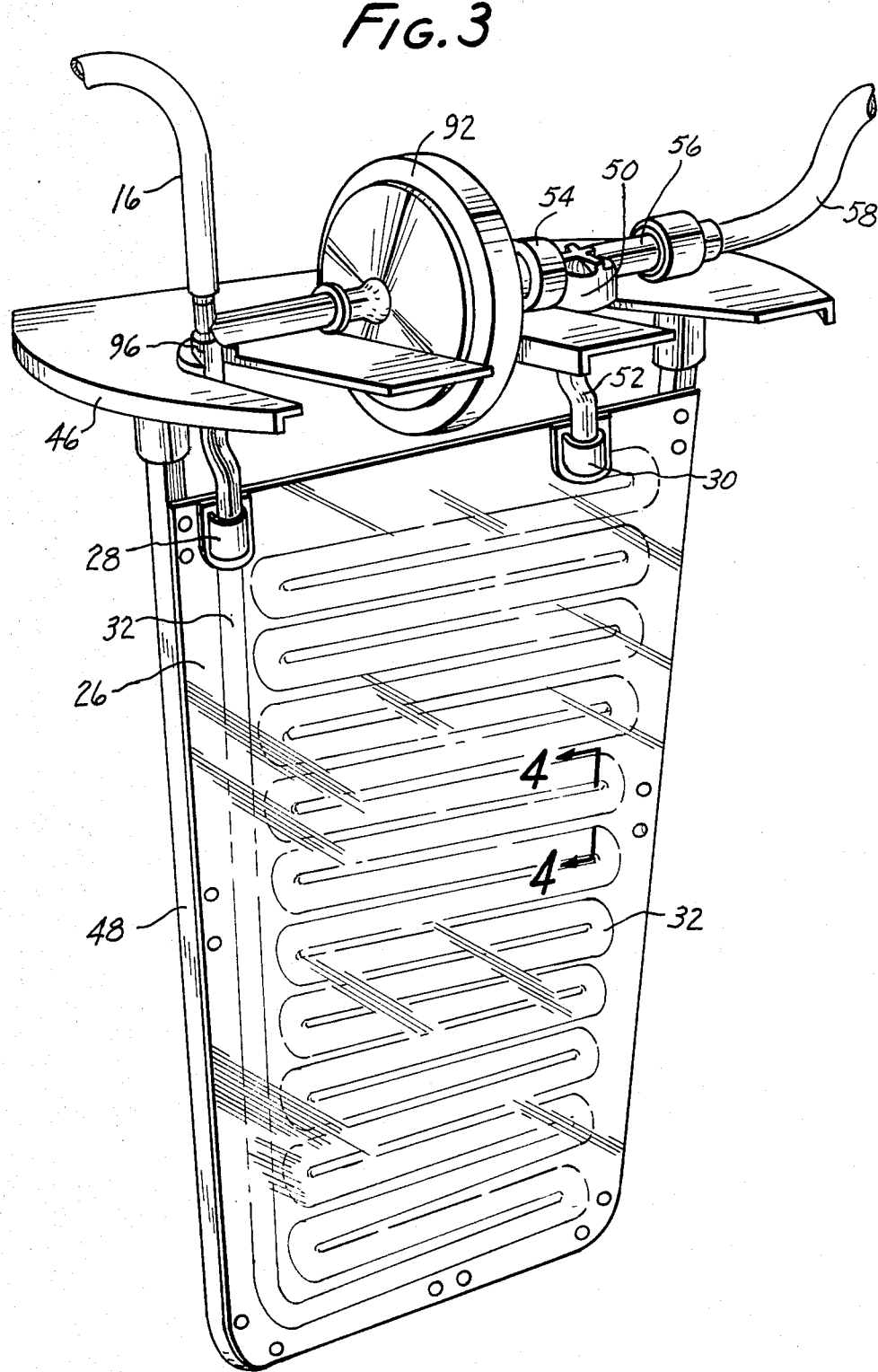
FIG. 3 is a perspective view of the flat plate heat exchanger assembly shown in FIG. 1.

The assembly herein which can be used in a thermodilution technique for measuring cardiac output is described with regard to the accompanying drawings wherein the thermodilution injectate assembly 10 is generally shown in FIG. 1. The components of the assembly 10 are schematically illustrated in FIG. 1 with a portion of the assembly shown in a partial exploded view to show how the components are assembled. As stated above in the background section, the assembly herein is designed for use in a thermodilution technique for measuring cardiac output. In such a technique a fluid is cooled, then injected into a patient and the time for the chilled fluid to flow from one location in the circulatory system of the patient to another and its dilution can be used to determine the cardiac output of the patient. The assembly includes an insulated container 12 which can be filled with a cooling agent or medium such as ice or a mixture of ice and water. Other cooling mediums can be used such as chemicals which undergo endothermic reactions. The cooling medium is utilized as a heat exchange source for cooling the fluid to be administered to the patient in determining cardiac output. The insulated container 12 can include a removable lid 14 which can be removed to introduce the cooling medium to the insulated container. The removable lid can be threadably or otherwise attached to the reservoir portion of the insulated container to provide a substantially effective heat seal between the lid and reservoir portion of the container. The insulated container can be provided with a support clamp 13 which can be used to support the insulated container such as on an intravenous stand 22.

Extending into the insulated container is a length of flexible tubing 16. Attached to one end of the flexible tubing is a puncture spike 18. The puncture spike can be inserted into the sealed port of an intravenous solution container such as the IV container 20. The IV container serves as the reservoir for the IV solution which is cooled and subsequently introduced into the circulatory system of the patient. The IV container can be a flexible or rigid container. The IV container can be supported on the IV stand 22 which also supports the insulated container. The IV container 20 shown in FIG. 1 is somewhat shown and drawn in a smaller scale than the overall assembly 10.

A clamp 24 can be positioned along the length of flexible tubing 16. The clamp can be actuated to permit or prevent fluid flow along the flexible tubing. The remaining end of the flexible tubing is connected to a heat exchanger 26 such as a flat plate heat exchanger positioned inside the insulated container and in heat exchange relationship with the cooling medium therein.

The heat exchanger 26 is also shown in FIG. 3. With regard to FIG. 3, the heat exchanger 26 includes an inlet port 28 wherein the fluid can be introduced to the heat exchanger and an outlet port 30 wherein the cooled fluid can exit the heat exchanger. A fluid-flow path 32 extends between the inlet and outlet ports. Preferably, the fluid-flow path 32 winds in a tortuous route through the heat exchanger 26. As can be seen in FIG. 3, the path can extend to the lower portion of the heat exchanger, then wind in a tortuous pathway back upwardly along the heat exchanger to provide exposure to a cooling medium in the insulated container.

The heat exchanger 26 is preferably a flat plate heat exchanger which is a laminated structure with one of the layers being a metal layer which performs as a heat transfer layer for placing the fluid flowing through the heat exchanger in a heat exchange relationship with the cooling medium. The laminated structure can be seen in FIGS. 4 and 5 which are views of two alternative embodiments as would be viewed taken along lines 4—4 of the heat exchanger shown in FIG. 3. In the embodiment shown in FIG. 4, the heat exchanger 26 comprises a metal layer 34 such as an aluminum layer which is contoured to provide a contoured fluid-flow path 36 therealong. A second layer 38 is sealed to the metal layer 34. The second layer can be another metal layer or can be a plastic layer such as a polyvinyl chloride, polyethylene and the like.

Another embodiment of the heat exchanger is shown in FIG. 5. In FIG. 5, the heat exchanger 26 is constructed of a first layer such as a metal layer 40 which is contoured to provide a fluid-flow path 44. The second layer 42 can be a metal layer or a plastic layer which is also contoured to provide a fluid-flow path, which contours align and coincide with the contours of the first metal layer 40 to provide the contoured fluid-flow path 44. Another embodiment of the heat exchanger is an embodiment wherein the first layer comprises an aluminum layer having a polyvinyl chloride coating about 0.001 inches thick along its contoured surface. Bonded to the polyvinyl chloride coating on the metal layer is a contoured polyvinyl chloride layer. The aluminum layer is from about 0.0025 to about 0.004 inches thick and the polyvinyl chloride layer is from about 0.005 to about 0.008 inches thick. The preferred heat exchanger is about 7 to 8 inches in length and from about 3½ to about 5½ inches in width and the fluid-flow pathway is from about 48 to about 60 inches in length.

As the heat exchanger 26 is a substantially flat plate, a heat exchanger support 46 (shown in FIG. 3) is used to provide support for the heat exchanger in the insulated container. The heat exchanger support 46 includes a support frame 48 which extends along the periphery of the heat exchanger 26 providing support for the easily bendable heat exchanger. The heat exchanger support 46 can be constructed of any suitable material for providing support and disposability to the assembly herein and is preferably constructed of a plastic such that the heat exchanger support and heat exchanger can be readily discarded after a single patient use.

The outlet port 30 of the heat exchanger is connected in fluid-flow communication with a dual directional valve 50. The dual directional valve is a three-ported valve having a first port 52, a second port 54 and a third port 56. The first port 52 is provided with a valve and seat therein which permits the flow of fluid into the body of the dual directional valve but which prevents fluid flow out of the first port. The second port 54 is provided with a valve and valve seat therein which permits fluid-flow out of such second port but prevents fluid flow into the dual directional valve through such second port. The third port 56 on the dual directional valve is not provided with a valve and thereby permits fluid flow out of and into the dual directional valve through such third port. Such a dual directional valve is disclosed in U.S. Pat. No. 4,210,173 of Choksi and Johnston, issued July 1, 1980, the entire disclosure of which is incorporated herein by this reference. As disclosed therein, and as can be utilized for the dual directional valve herein, the valves in the first and second ports can be check valves which comprise flexible, resilient disks which are urged against their respective valve seats by central pressure posts. A greater biasing can be provided against the check valve in the second port 54 (the outlet check valve) than is provided against the check valve in the first port (the inlet check valve).

The third port 56 of the dual directional valve is connected to a length of insulated flexible tubing 58. Insulated flexible tubing is preferred as the fluid flowing through the tubing has been cooled and it is desired to maintain the fluid in such a cool condition. Such insulated flexible tubing is illustrated in cross section in FIG. 2 which is a view taken along lines 2—2 of FIG. 1. The insulated flexible tubing 58 includes a sidewall 60 and an inner lumen 62 which provides the fluid flow generally centrally and axially along the tubing. Within the sidewall 60 is a plurality of secondary lumens which can be air-filled to provide insulating capacity to the sidewall. Rather than lumens, a plurality of air pockets can be provided in the sidewall of the insulated flexible tubing.

The end of the insulated flexible tubing is connected to a three-ported stopcock 66. The three-ported stopcock can be provided with a handle and core 67 which can be positioned to open or close the ports to fluid flow. A first port 68 of the three-ported stopcock can be connected to the insulated flexible tubing 58. A second port 70 of the three-ported stopcock can be connected to a syringe 74. The syringe can be a conventional syringe of a suitable size for administering the cooled fluid to the patient in an appropriate volume. In the preferred embodiment shown in FIG. 1, the syringe is an insulated syringe. The insulated syringe has a dead air space between the syringe barrel and a sleeve which extends around the barrel. The insulated syringe prevents any appreciable warming of the fluid while the fluid is in the syringe. Generally, such a syringe is a 5 to 10 cc syringe. For such a large size syringe, the plunger can be provided with a larger hand or palm engaging comfort pad to provide administering such a relatively large volume of fluid and can be provided with enlaraged finger grips.

There can be positioned between the three-ported stopcock 66 and the syringe 74 a Y or T adapter 76. One of the ports on the adapter can be connected to the syringe while another port can be provided with a temperature probe 78 which can monitor the temperature of the fluid as it is being administered to the patient. The temperature probe 78 can be connected through suitable electrical connection such as the temperature probe lead 80 to a display unit 82. A syringe clamp 75 can be provided on the insulated container to support the syringe 74.

The third port 72 on the three-ported stopcock can be connected to another length of flexible tubing 84. The length of flexible tubing 84 can also be an insulated flexible tubing such as the insulated flexible tubing 58. The flexible tubing 84 is connected to a catheter 88 which is inserted into a patient 86. In a preferred embodiment and to provide less opportunity for warming of the fluid, the third port can be connected directly to the catheter 88. The catheter is generally a catheter having a temperature probe located adjacent its tip and which provides an opening of the lumen extending through the catheter spaced apart from the tip. When the catheter is implanted in the patient, the opening of the lumen is upstream of the catheter tip such that when the cooled fluid is introduced through the catheter it exits the lumen through such an opening, then flows through the circulatory system toward the catheter tip and temperature probe in the catheter tip. Such catheters are commercially available and the commercially available catheters are acceptable for use herein. Commercially available catheters include the series of Swan-Ganz catheters available from American Edwards Laboratories.

A catheter temperature probe lead 90 extends from the catheter to the display unit 82. The display unit 82 can contain appropriate circuitry to convert the temperature of the fluid injected into the patient sensed by the temperature probe 78 and the temperature sensed by the temperature probe at the catheter tip to a cardiac output using an appropriate algorithm. The cardiac output can be displayed by the display unit 82.

The assembly herein provides a return circuit for fluid. That is, the assembly provides the ability to return fluid which has been cooled to the cooling path in the event such fluid has been warmed. The three-ported stopcock is closed to fluid flow to the catheter. The return path is along the insulated flexible tubing 58 and through the dual directional valve 50. The fluid flows through the dual directional valve and through the second port 54 to the inlet port 28 of the heat exchanger 26. There can be positioned between the second port 54 of the dual directional valve and the inlet flexible tubing leading to the heat exchanger a filter housing 92 which contains a microporous filter. Such a microporous filter prevents the introduction of microparticles which may have been absorbed by the fluid along the system and prevents the reintroduction of such microparticles to the fluid. The filter housing can be provided with openings 94 which are covered by a hydrophobic filter inside the filter housing. Such a hydrophobic filter provides for the escape of air or other gases from the fluid while preventing any fluid from flowing out of the filter housing. A connector such as T or Y connector 96 can be connected to the inlet port of the heat exchanger to connect the flexible tubing 16, the return flow path through the filter housing 92 and the inlet port 28.

To return warmed fluid to the cooling system, the three-ported stopcock is closed to fluid flow to the catheter and upon actuating the syringe, the warmed fluid flows through the insulated tubing, the dual directional valve, filter, T-connector and flexible tubing and is returned to the solution container. Upon withdrawing the syringe plunger, fresh cooled fluid is drawn through the heat exchanger and into the syringe.

The catheter extending into and implanted in the patient 86 can include an additional lumen for the introduction of medication or for inflating a balloon on the catheter. Such an additional lumen can be connected to a syringe such as a syringe 98.

The thermodilution injectable assembly herein is used by filling the insulated container with an ice solution, then immersing the support and heat exchanger into such an ice bath. The heat exchanger can be positioned first within the insulated container, then the container filled with a heat exchanger medium; i.e., ice bath. The lid is then placed on the insulated container. The puncture spike 18 is inserted through the puncturable seal of an IV solution bag 20 and the solution permitted to drain through the puncture spike 18 and through the flexible tubing 16 into the heat exchanger.

The fluid flows through the fluid-flow path in the heat exchanger in a heat exchanger relationship with the ice bath in the insulated container. As the fluid flows along the tortuous path of the heat exchanger, there is heat exchange across the metal layer and the fluid is cooled. As the fluid exits the outlet port, it flows through the dual directional valve and along the insulated flexible tubing 58. The fluid can be drawn through the heat exchanger and insulated flexible tubing by the action of withdrawing the plunger of the syringe which draws the fluid into the body of the syringe. For the fluid to flow into the syringe, the stopcock handle 67 can be positioned to close the third port 72 of the three-port stopcock and open the first and second ports to fluid flow. When the fluid has accumulated in the syringe to the desired volume, the handle of the three-ported stopcock is positioned to close the first port to fluid flow, thereby opening the second and third ports to fluid flow. The plunger of the syringe is actuated to cause the fluid in the syringe to flow along the flexible tubing 84 and into the patient through the catheter 88.

The fluid flows out of the catheter and into the circulatory system of the patient and then along and past the temperature probe at the catheter tip. The temperature of the fluid as it is introduced and the temperature sensed by the temperature probe at the catheter tip are relayed to the display unit which can calculate and display the cardiac output of the patient.

In the event additional fluid is retained in the syringe and warms to a temperature unsuitable for administering to the patient, the handle of the three-ported stopcock can be positioned to close the third port and open the first and second ports to fluid flow. The fluid can then be forced from the syringe along the insulated flexible tubing back to the dual directional valve. The fluid enters the dual directional valve, encounters resistance against the valve in the first port, and flows through the valve in the second port. The fluid flows through such second port into and through the filter in the filter housing and into the inlet flexible tubing leading to the heat exchanger and then back into the solution container. The fluid can then be reintroduced to the heat exchanger and recooled for subsequent administration to the patient.

What is claimed is:

1. An assembly for use in a thermodilution technique for measuring cardiac output, the assembly comprising:
    (a) fluid introductory means for connecting the assembly to a source for fluid to be cooled and administered to a patient;
    (b) an insulated container means for holding a heat exchange medium which can exchange heat with the fluid flowing through the assembly;
    (c) a heat exchanger means positioned in the insulated container means having an inlet port in fluid-flow communication with the fluid introductory means and an outlet port with a closed fluid-flow path means extending between the inlet port and outlet port for providing a pathway for the fluid to be administered to the patient in heat exchange relationship with the heat exchange medium;

(d) a dual directional valve means in fluid-flow communication with the outlet port of the heat exchanger means for directing fluid to the patient or returning fluid to the fluid introductory means;

(e) a three-ported stopcock in fluid-flow communication with the dual directional valve means through one of the three ports;

(f) a syringe connected to one of the ports on the three-ported stopcock; and (g) fluid delivery means connected to a port on the three-ported stopcock for delivering fluid to a patient by connecting such fluid delivery means to a catheter which can be inserted in a patient for introducing fluid to the patient, which catheter includes temperature monitoring means for monitoring temperature in the circulatory system of the patient.

2. An assembly as recited in claim 1 wherein the heat exchanger means comprises a substantially flat plate heat exchanger having fluid-flow path extending therethrough.

3. An assembly as recited in claim 1 wherein the heat exchanger means comprises a flat plate laminate including at least one layer of heat-conducting metal having a fluid-flow path contoured therein and a second layer sealed to such metal layer and enclosing such contoured fluid-flow path.

4. An assembly as recited in claim 3 wherein the second layer comprises a heat-conducting metal.

5. An assembly as recited in claim 3 wherein the heat-conducting metal layer comprises an aluminum layer.

6. An assembly as recited in claim 3 wherein the second layer comprises a plastic layer sealed to the metal layer.

7. An assembly as recited in claim 6 wherein the plastic second layer comprises a polyvinyl chloride layer.

8. An assembly as recited in claim 3 comprising a corresponding fluid-flow path contoured in the second layer, which fluid-flow path coincides with the contoured fluid-flow path extending along the metal layer.

9. An assembly as recited in claim 8 wherein the second layer comprises a heat-conducting metal.

10. An assembly as recited in claim 8 wherein the second layer comprises a plastic layer sealed to the metal layer.

11. An assembly as recited in claim 10 wherein the plastic second layer comprises a polyvinyl chloride layer.

12. An assembly as recited in claim 1 wherein the dual directional valve means comprises a three-ported valve body wherein a first port has a valve positioned therein for permitting fluid flow into the valve body and preventing fluid flow out of the valve body, a second port has a valve positioned therein for permitting fluid flow out of the valve body and preventing fluid flow into the valve body, and a third port permitting fluid flow into and out of the valve body.

13. An assembly as recited in claim 12 wherein the first port of the dual directional valve means is in fluid-flow communication with the outlet port of the heat exchanger means, the second port of the dual directional valve means is in fluid-flow communication with the fluid introductory means, and the third port of the dual directional valve means is in fluid-flow communication with a port on the three-ported stopcock.

14. An assembly as recited in claim 13 further comprising filter means positioned between the second port of the dual directional valve means and the fluid introductory means for filtering fluid flowing from the dual directional valve means to the fluid introductory means.

15. An assembly as recited in claim 14 wherein the filter means comprises a filter housing having openings therein, a microporous filter medium for filtering fluid flowing through the filter housing and a hydrophobic filter medium inside the housing and covering the openings in the filter housing for preventing fluid flow out of the housing through such openings.

16. An assembly as recited in claim 1 further comprising temperature sensing means for sensing the temperature of fluid in the assembly, which temperature sensing means is positioned between the heat exchanger means and the patient.

17. An assembly as recited in claim 16 wherein the temperature sensing means comprises a temperature probe positioned between the syringe and the three-ported stopcock and the syringe comprises an insulated syringe.

18. An assembly as recited in claim 17 further comprising a Y-connector positioned between the three-ported stopcock and syringe wherein the syringe is connected to one of the ports of the Y-connector and the temperature probe is connected to a port on the Y-connector.

19. An assembly as recited in claim 1 further comprising a length of insulated flexible tubing having one end connected to the dual directional valve means and one end connected to a port on the three-ported stopcock.

20. An assembly as recited in claim 19 wherein the length of insulated tubing comprises tubing having a sidewall and interior lumen wherein air is encapsulated in the sidewall.

21. An assembly as recited in claim 20 wherein the length of insulated tubing comprises a length of flexible tubing having a plurality of lumens extending therethrough wherein one lumen extends generally centrally of the tubing for fluid flow and a plurality of lumens extend through the sidewall generally parallel to the central lumen.

22. An assembly as recited in claim 1 wherein the insulated container means comprises a reservoir portion and a removable cover portion.

23. An assembly as recited in claim 22 wherein the cover portion further comprises a clamp on its outer surface for holding the syringe.

24. An assembly as recited in claim 1 further comprising a support for fitting within the insulated container means for supporting the heat exchanger means in the insulated container means.

25. An assembly as recited in claim 24 wherein the support further comprises a conduit for connecting the fluid introductory means to the inlet port of the heat exchanger means and a conduit for connecting the dual directional valve means to the outlet port of the het exchanger means.

26. An assembly as recited in claim 1 wherein the fluid introductory means comprises a length of flexible tubing connected at one end to a puncture spike means for puncturing a seal on a solution container and at one end to a connector which in turn is connected to the inlet port of the heat exchanger and to the dual directional valve means.

27. An assembly for use in a thermodilution technique for measuring cardiac output, the assembly comprising:
  (a) a length of flexible tubing having a puncture spike connected to one of its ends, which puncture spike can puncture a puncture port of an intravenous solution container and a three-ported connector connected to its other end;
  (b) a substantially flat plate heat exchanger means having an inlet port connected to the flexible tubing through such three-ported connector and an outlet port with a closed fluid-flow path means extending between the inlet port and outlet port for providing a heat exchange relationship between a fluid flowing through the fluid-flow path through the flat-plate heat exchanger means and a heat exchange medium surrounding the flat plate heat exchanger means;
  (c) an insulated container extending around and supporting the flat plate heat exchanger means, which insulated container can be filled with a heat exchange medium;
  (d) a three-ported dual directional valve wherein a first port is in fluid-flow communication with the outlet port of the flat plate heat exchanger means and wherein such first port includes a valve positioned therein for permitting fluid flow into the dual directional valve and preventing fluid flow into the outlet port of the flat plate heat exchanger means, a second port in fluid-flow communication with the three-ported connector, which second port includes a valve positioned therein for permitting fluid flow out of the dual directional valve and preventing fluid flow into the dual directional valve, and a third port permitting fluid flow into and out of the dual directional valve;
  (e) a three-ported stopcock in fluid-flow communication with the third port of the dual directional valve through one of the three ports on the three-ported stopcock;
  (f) an insulated syringe connected to one of the ports on the three-ported stopcock; and
  (g) a length of flexible tubing connected to a port on the three-ported stopcock for delivering fluid to a patient by connecting such length of flexible tubing to a catheter which can be inserted in a patient, which catheter includes temperature monitoring means for monitoring temperature in the circulatory system of the patient.

28. An assembly as recited in claim 27 wherein the flat plate heat exchanger means comprises a laminate including at least one layer of heat-conducting metal having a fluid-flow path contoured therein and a second layer sealed to such metal layer and enclosing such contoured fluid-flow path.

29. An assembly as recited in claim 27 wherein the heat-conducting metal layer comprises a laminated structure including a plastic layer extending over an aluminum layer.

30. An assembly as recited in claim 29 wherein the second layer comprises a plastic layer sealed to the heat-conducting metal layer.

31. An assembly as recited in claim 30 wherein the plastic second layer comprises a polyvinyl chloride layer.

32. An assembly as recited in claim 27 comprising a corresponding fluid-flow path contoured in the second layer, which fluid-flow path coincides with the contoured fluid-flow path extending along the metal layer.

33. An assembly as recited in claim 27 further comprising a Y-connector positioned between the three-ported stopcock and syringe wherein the syringe is connected to one of the ports of the Y-connector and a temperature probe is connected to a port on the Y-connector.

34. An assembly as recited in claim 27 further comprising a length of insulated flexible tubing having one end connected to the dual directional valve means and one end connected to a port on the three-ported stopcock.

35. An assembly for use in a thermodilution technique for measuring cardiac output, the assembly comprising:
  (a) a length of flexible tubing having a puncture spike connected to one of its ends, which puncture spike can puncture a puncture port of an intravenous solution container and a three-ported connector connected to its other end;
  (b) a substantially flat plate heat exchanger comprising a laminated structure wherein at least one layer of the laminated structure comprises a heat-conducting metal having a fluid-flow path contoured therein and a second layer sealed to such metal layer and enclosing such contoured fluid-flow path, an inlet port in fluid-flow communication with the length of flexible tubing through such a three-ported connector and an outlet port in fluid-flow communication with the contoured fluid-flow path;
  (c) an insulated container extending around and supporting the flat plate heat exchanger, which insulated container can be filled with a heat exchange medium;
  (d) a three-ported dual directional valve wherein a first port is in fluid-flow communication with the outlet port of the flat plate heat exchanger and wherein such first port includes a valve positioned therein for permitting fluid flow into the dual directional valve and preventing fluid flow into the outlet port of the flat plate heat exchanger, a second port in fluid-flow communication with the three-ported connector, which second port includes a valve positioned therein for permitting fluid flow out of the dual directional valve and preventing fluid flow into the dual directional valve, and a third port permitting fluid flow into and out of the dual directional valve;
  (e) a filter housing including a microporous filter medium therein, which filter housing is connected in fluid-flow communication between the second port of the dual directional valve and three-ported connector;
  (f) a three-ported stopcock in fluid-flow communication with the third port of the dual directional valve through one of the three ports on the three-ported stopcock;
  (g) an insulated syringe connected to one of the ports on the three-ported stopcock; and
  (h) a length of flexible tubing connected to a port on the three-ported stopcock for delivering fluid to a patient by connecting such length of flexible tubing to a catheter which can be inserted in a patient, which catheter includes temperature monitoring means for monitoring temperature in the circulatory system of the patient.

36. An assembly as recited in claim 35, wherein the heat-conducting metal layer comprises a laminated layer of an aluminum layer and a plastic layer.

37. An assembly as recited in claim 36 wherein the second layer comprises a plastic layer sealed to the plastic layer of the heat-conducting metal layer.

38. An assembly as recited in claim 37 wherein the plastic layers comprise polyvinyl chloride layers.

39. An assembly as recited in claim 35 comprising a corresponding fluid-flow path contoured in the second layer, which fluid-flow path coincides with the contoured fluid-flow path extending along the metal layer.

* * * * *